(12) United States Patent
Bolla

(10) Patent No.: US 7,878,997 B2
(45) Date of Patent: Feb. 1, 2011

(54) MALLET FINGER SPLINT

(75) Inventor: Kalman Bolla, Neuhausen (CH)

(73) Assignee: Chrisofix AG (CH)

( * ) Notice: Subject to any disclaimer, the term of this patent is extended or adjusted under 35 U.S.C. 154(b) by 346 days.

(21) Appl. No.: 12/067,038

(22) PCT Filed: Sep. 8, 2006

(86) PCT No.: PCT/CH2006/000482

§ 371 (c)(1),
(2), (4) Date: Mar. 14, 2008

(87) PCT Pub. No.: WO2007/030962

PCT Pub. Date: Mar. 22, 2007

(65) Prior Publication Data

US 2008/0255487 A1    Oct. 16, 2008

(30) Foreign Application Priority Data

Sep. 16, 2005   (CH) .................................. 1515/05

(51) Int. Cl.
*A61F 5/00* (2006.01)
(52) U.S. Cl. .......................................... 602/20; 602/22
(58) Field of Classification Search ............. 602/20–23; 128/877–880; 482/47–48
See application file for complete search history.

(56) References Cited

U.S. PATENT DOCUMENTS

| | | | |
|---|---|---|---|
| 2,548,378 A * | 4/1951 | Kleinfeld ..................... | 602/22 |
| 4,161,175 A * | 7/1979 | Bentele ......................... | 602/6 |
| 4,502,690 A * | 3/1985 | Ruperto ...................... | 473/513 |
| 4,798,199 A | 1/1989 | Hubbard ...................... | 602/21 |
| 5,031,608 A | 7/1991 | Weinstein | |
| 5,230,699 A | 7/1993 | Grasinger .................... | 602/22 |
| 5,479,708 A * | 1/1996 | Thomas ....................... | 30/122 |
| 5,681,269 A * | 10/1997 | Basaj et al. ................... | 602/22 |
| 6,520,925 B1 | 2/2003 | Thibodo, Jr. | |
| 6,575,925 B1 * | 6/2003 | Noble .......................... | 602/20 |
| 6,692,452 B2 | 2/2004 | Chow ........................... | 602/5 |

FOREIGN PATENT DOCUMENTS

CH    689820    12/1995

OTHER PUBLICATIONS

International Search Report dated Apr. 23, 2007.

* cited by examiner

Primary Examiner—Michael A. Brown
(74) Attorney, Agent, or Firm—Ostrolenk Faber LLP

(57) ABSTRACT

The invention relates to a mallet finger splint for splinting the distal and middle phalanx of a mallet finger in a position in which the first finger joint is held in an extended position between the distal phalanx and the middle phalanx. The aim of the invention is to simplify production and use of such a finger splint. For this purpose, the mallet finger splint has a shape of a spoon with a handle and a bowl. The mallet finger splint is configured in such a manner than the handle comes to rest below the middle phalanx without impairing the mobility of the middle finger joint while the distal phalanx comes to rent in the bowl.

5 Claims, 5 Drawing Sheets

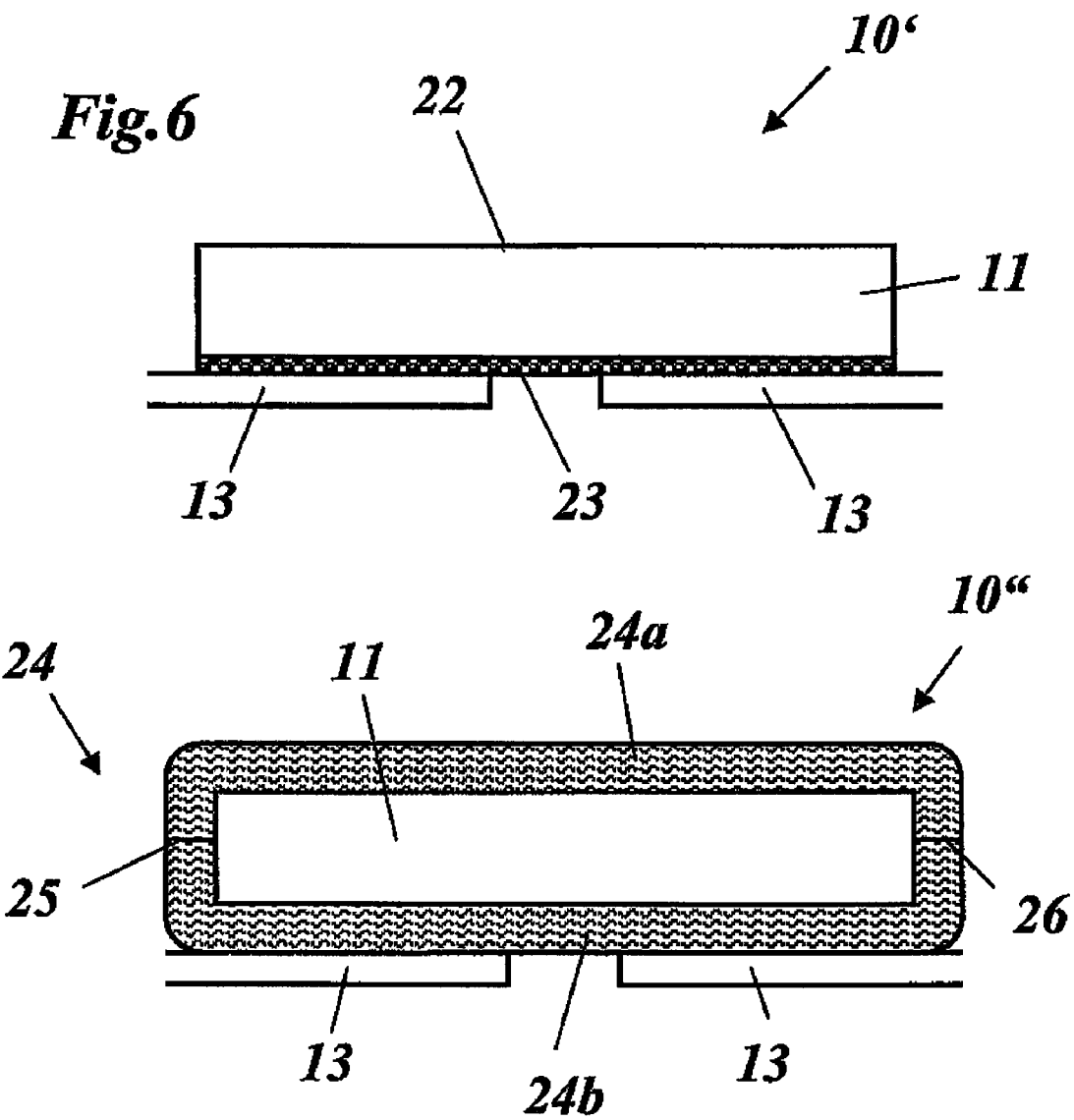

MALLET FINGER SPLINT

CROSS REFERENCE TO RELATED APPLICATIONS

The present application is a 35 U.S.C. §371 National Phase conversion of PCT/CH2006/000482 filed Mar. 22, 2007, which claims priority of Swiss Application No. 1515/05 filed Sep. 16, 2005.

TECHNICAL FIELD

The present invention relates to the field of medical splints. It concerns a mallet finger splint according to the preamble of claim 1.

STATE OF THE ART

A mallet finger or dropped finger or baseball finger is to be understood as a finger injury with which the mechanism which extends the finger at its front end (at the first (distal) finger joint) between the first phalanx and the middle phalanx), is interrupted. This type of finger injury occurs for example when a ball impinges directly on the finger tip with great impact (with baseball or other ball games).

Special mallet finger splints are applied for the therapy of such a finger injury, which fix the injured finger in the extended position with a first phalanx slightly bent up. Various types of mallet finger splints are known from the state of the art, which each entail certain disadvantages.

A mallet finger splint is described in DE-U1-84 32 615, which consists of a shell supporting the outermost finger joint and the first phalanx on the underside, and of a shell supporting the outer (distal) finger joint and the middle phalanx on the upper side, which are connected to one another in a tubular manner, wherein the shell on the underside is cut out in a defined maimer. Such tubular splints are shape-stable, simple in manufacture and application, and provide support to the injured finger on all sides. The disadvantage however, is the fact that these splints are stiff and may not be adapted. One thus needs to manufacture and keep in stock splint sizes for differently large fingers, in order to achieve an adequate fixation by way of a good adaptation. The same applies to the finger splint disclosed in DE-A1-35 17 073.

A mallet finger splint is known from GB-929 317, which is composed of several sheet metal parts which may be connected to one another in an adjustable manner, in order to be adapted to differently long fingers. By way of this, it is possible to splint differently large fingers with a set of parts. The disadvantage is however the comparatively expensive manufacture and complicated handling, with which firstly the sheet metal parts are assembled, then the padding applied, and finally the splint must be fastened to the finger.

A mallet finger splint is disclosed in U.S. Pat. No. 6,692, 452, which consists of a flexible tube which may be stuck over the finger and which on the lower side comprises a pocket into which a shape-providing stiff plate of a suitable plastic material may be inserted. Here too, there exits the problem of the flexible tube sitting in a manner which is too tight or too loose given differently thick fingers, or otherwise of flexible tubes with different diameters having to be used.

U.S. Pat. No. 5,925,008 shows a mallet finger splint which consists of an angled splint part which is arranged on the upper side of the finger and which is connected to the injured finger with bandages wound around the finger and splint part. Despite the construction being simple and an adaptability to different finger sizes being provided, the application turns out to be rather difficult, since here, different, separate bandages need to be applied, in order to achieve the desired extended position of the finger by way of a tight connection between the splint part and the finger.

Finally, a mallet finger splint is known from US-A1-2005/0027223, which consists of three separate shell-like segments which are connected to one another by a stiff wire in a manner such that it may be adjusted in length and angle, and which are assigned to the individual phalanxes. The rail is fastened on the first and last phalanx by way of Velcro-type-type strips. Such a splint requires some effort with regard to manufacture on account of the complicated mechanical construction, and is bothersome to the finger.

A finger splint with a so-called baseball configuration is disclosed in the document U.S. Pat. No. 6,575,925, which consists of an elongate shell of aluminum, plastic or foam, on whose upper side a rest surface is arranged, and which is fastened by way of a strip or several strips with a Velcro-type closure, which closed in themselves, are led in each case through an eyelet on the underside of the splint and over the finger lying on the splint. Although a spoon-shape is mentioned in the description, the splint on the underside of the finger has a uniformly large width. Furthermore, it extends from the distal end of the finger to the proximal end directly at the transition to the palm of the hand. A multitude of disadvantages arise from this:

The length of the splint going over all phalanxes, unnecessarily significantly compromises the movement possibility of the splinted finger. In particular, the finger may not be bent at the innermost (proximal) joint and at the middle joint.

The large width of the splint extending over the whole length of the finger also compromises the movement ability of the adjacent unsplinted finger.

The eyelets attached on the underside of the splint, for threading through the fastening tape, are of a hindrance when using the hand, since they may snag behind objects. They render the manufacture and application of the splint more complicated, and they prevent the splint from being able to be manufactured with a sheath. Moreover, they are of a hindrance with regard to the adaptation of the splint to a finger.

The Velcro-type strip which is closed in itself, for fastening, has a hook surface at one end, and this surface faces the finger and may therefore compromise the wearing comfort.

A further general problem with known mallet finger splints, is that the splints tend to slip, so that the desired over-extended support of the injured finger is only ensured to a limited extent. It is therefore desirable with an improved mallet finger splint, to also remedy this problem.

Concluding, one may say that the known mallet finger splints have the following disadvantages:

The splints extend usually not only over the outer (distal) finger joint, but also over the middle finger joint and mostly reach up to the palm. By way of this, the possibility of movement of the splinted finger is greatly restricted, without this being of use to the actual splinting.

If the splints reach up to the palm, an outwardly acting force in the longitudinal direction of the splint is exerted onto the rear end of the splint by way of a bending of the splinted finger at the inner (proximal) finger joint, and this force may lead to a displacement of the splint relative to the finger (forward slipping), and compromises the effect of the splint.

The known splints assume much space, which not only limits the movement ability of the splinted finger, but also the movement space of the other fingers of the same hand.

This also applies to the fastening means, with which the finger splint is fastened on the finger. These fastening means are often voluminous, uncomfortable and difficult to handle.

DESCRIPTION OF THE INVENTION

It is therefore the object of the invention, to specify a mallet finger splint, which is simply constructed and manufactured, is rapid and uncomplicated in application, is characterized by low dimensions and a low weight, and offers a large wearing comfort with as little as possible movement limitations, and is secured against unintended slipping of the finger.

This object is achieved by the entirety of the features of claim 1. The core of the invention lies in giving the mallet finger splint the shape of a spoon with a short handle and a slightly upwardly bent shell, wherein the mallet finger splint is designed in a manner such that the handle lies below the middle phalanx, without compromising the movement of the middle finger joint, whilst the front finger phalanx comes to lie in the shell. The shell provides a trough into which the first phalanx may be securely and comfortably applied in the extended position of the front finger joint, whilst the handle in cooperation with the middle phalanx assumes the fixation of the splint on the finger. The finger splint according to the invention may be designed very short and lightweight, and may be very easily fastened on account of the handle. Since the handle is kept so short that it does not compromise the movement ability of the middle finger joint, no longitudinal force is exerted onto the splint on bending the middle finger joint, and any slipping of the splint relative the finger is securely avoided on account of this.

One design of the mallet finger splint according to the invention is characterized in that means for the releasable fastening of a fastening tape are provided at least on the outer side of the handle and these preferably comprise hooks in the manner of a Velcro-type type closure. It is possible by way of this, to use a simple, in particular textile fastening tape which is wrapped around the finger and is releasably fastened with both ends on the outer side of the handle, for the fastening of the splint which is to be worn in a secure and comfortable manner.

In order to secure the splint even more effectively against a slipping, it may be advantageous if means blocking a slipping are provided on the mallet finger splint, which block a relative displacement between the mallet finger splint and the fingers. In this manner, the finger splint remains securely in its position relative to the finger, independently of the forces acting on it from the outside.

The mallet finger splint is particularly designed as one piece.

According to a preferred further formation of the invention, the mallet finger splint is formed of a sheet metal, preferably an aluminum sheet part is used as sheet metal.

In order for the finger splint to be able to be adapted to the finger in certain limits given an adequate stiffness, it is advantageous if the sheet metal is plastically deformable by hand, and if corrugations are formed in the sheet metal for longitudinal stiffening, whose crests run in the longitudinal direction of the splint or of the finger. The sheet metal may additionally be perforated for an improved breathing activity.

The sheet metal may be covered with at least one layer on the inner side and/or on the outer side, for increasing the comfort and for providing further functions such as an improved slippage prevention. In particular, the sheet metal on both sides is covered with an intermediate layer of plastic foam, in particular PU foam, and a further cover layer which assumes the additional functions, is arranged in each case on the intermediate layers.

The intermediate layers are preferably bonded to the sheet metal e.g. with a hot-melt adhesive, and the intermediate layers and the associated cover layers are in each case laminated together.

It is advantageous for the wearing comfort and the simple handling, if the inner cover layer consists of a textile material leading away the sweat, and the outer cover layer consists of a textile material which is suitable for a Velcro-type closure. The inner cover layer may be additionally provided with a function preventing the reproduction of sweat bacteria.

Preferably, a fastening tape is provided for fastening the mallet finger splint on the finger, and this tape with both ends is releasably fastened on the handle and encloses the middle phalanx lying thereon, wherein a Velcro-type closure is arranged on the mallet finger splint, in particular on the outer side of the handle, for fastening the fastening tape on the mallet finger splint. Such a fastening is extremely space-saving, is simple to handle and comfortable to wear, since the fastening tape adapts to the finger and lies softly on the finger.

It is favorable for slippage-prevention means to comprise a double adhesive strip bonded onto the upper layer of the handle, in order to prevent a slipping of the finger splint along the finger.

A further improvement results if additional slippage-prevention means are arranged on the fastening tape for fixing the fastening tape relative to the finger, said additional slippage-prevention means preferably comprising a double-sided adhesive tape and coming to lie on the upper side of the finger when the fastening strip is wound around the finger.

The mallet finger splint may however also be formed of plastic, wherein then preferably a hook layer as part of a Velcro-type closure is attached preferably on the outer side of the handle.

According to another design, the mallet finger splint comprises a sheath which comprises an upper ply and a lower ply, wherein the finger to be splinted comes to lie on the upper ply and the lower ply covers the mallet finger splint on the lower side. Advantageously, the upper ply has slippage-prevention properties, and in particular comprises silicone, preferably in the form of embedded balls. The lower ply is preferably designed as the part of a Velcro-type closure containing hooks.

BRIEF DESCRIPTION OF THE FIGURES

The invention is hereinafter described in more detail by way of embodiment examples in combination with the drawings. There are shown in FIG. 1 in a perspective lateral view, one embodiment example of the mallet finger splint according to the invention, with a fastening tape;

FIG. 6 in a cross section through the handle, a mallet finger splint formed of plastic, according to another embodiment example of the invention, with a hook layer which is formed on the lower side of the handle and which serves for fastening the two ends of a fastening tape;

FIG. 7 in a cross section through the handle, a mallet finger splint according to a further embodiment example of the invention, which is accommodated in a sheath consisting of an upper ply and a lower ply, which serves for preventing slippage and for fastening the fastening tape;

WAYS OF CARRYING OUT THE INVENTION

Figure 1:
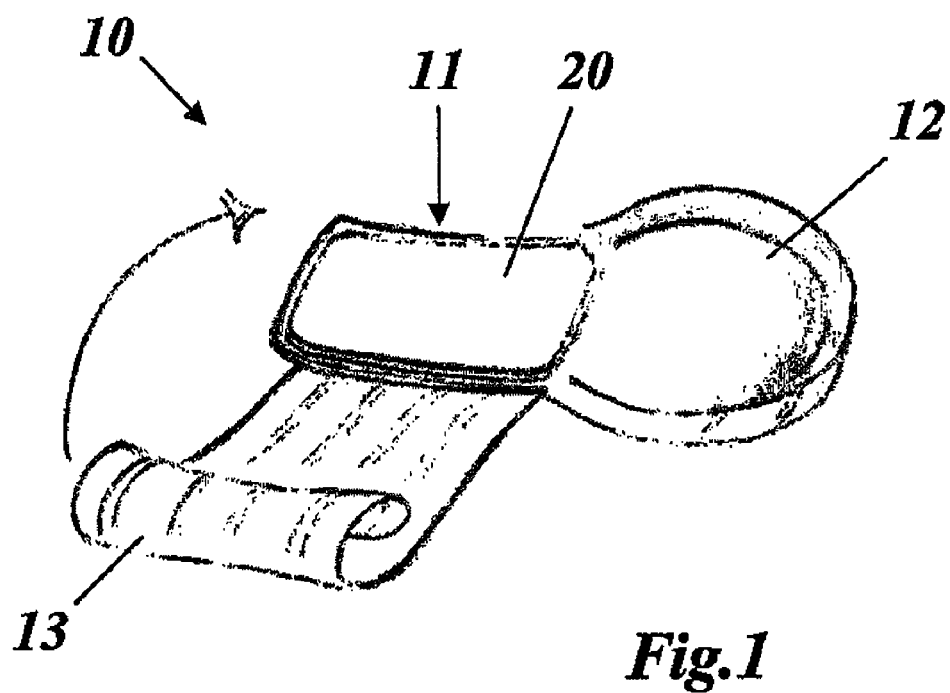

One embodiment example of a mallet finger splint according to the invention is represented in FIG. 1 in a perspective lateral view. The mallet finger splint 10 has the general shape of a short-handled spoon with a flat handle 11 and a concave shell 12 connecting thereto. The mallet finger splint 10 with its spoon shape, is designed in a manner such that according to FIG. 2, with a splint attached on a finger F, the handle 11 lies below the middle (medial) phalanx F2, whilst the front (distal) phalanx F1 comes to lie in the shell 12. The shell 12 is bent slightly upwards with respect to the handle 11, so that the front finger joint 29 is held in an extended position between the front (distal) phalanx F1 and the middle (medial) phalanx F2. The position of the shell 12 relative to the handle 11 may however be adapted and changed on account of the flexibility of the splint. Likewise, the lateral edges of the shell 12 may be bent up to a greater degree, in order to give the splinted finger F more lateral support.

Figure 2:
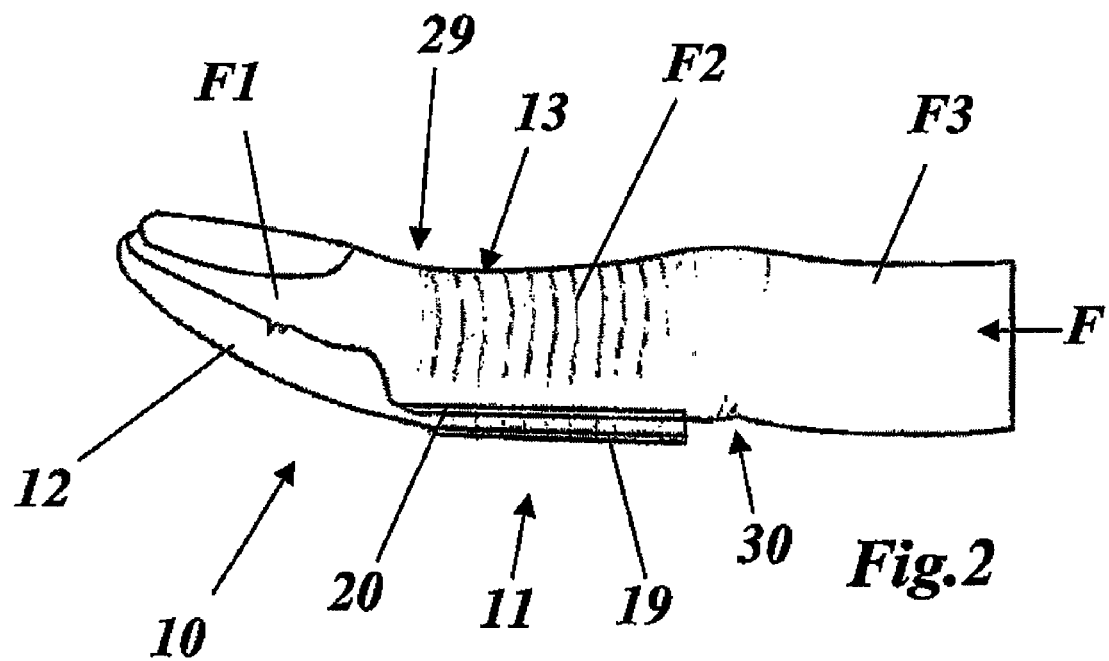
FIG. 2 a mallet finger splint according to FIG. 1, attached on a finger.

The length of the handle 11 according to FIG. 2 is adapted to the length of the middle (medial) phalanx 2. The mallet finger splint 10 extends thus only over the two front phalanxes F1 and F2. The rear (proximal) phalanx F3 on the other hand remains free. The mallet finger splint 10 is designed as one piece and may thus be easily manufactured and applied. The basic element of the mallet finger splint 10 is an aluminum sheet 14 which extends through the handle 11 and the shell 12. The thickness of the sheet 14 is selected (a few 1/10 of a millimeter, preferably between 0.2 and 0.6 mm), such that the sheet 14 may be plastically deformed by hand, so that the mallet finger splint 10 in particular in the region of the shell 12, may be adapted to the respective finger F or the phalanxes F1, F2. In order, despite the (limited) deformability, to achieve a stiffness which is necessary for the splinting, corrugations are formed into the sheet 14 for longitudinal stiffening, whose crests run in the longitudinal direction of the splint or of the finger F. A comparable sheet (with a different orientation of the corrugations) has already been suggested with different splints by the same applicant (EP-B1-0 874 607).

Several layers which assume different functions with regard to wearing comfort and fastening of the splint are attached above the sheet on the upper and lower side. With this, the mallet finger splint 10 has the construction represented in FIG. 5 in the region of the handle 11. The central corrugated aluminum sheet 14 is bonded on both sides to an intermediate layer 15 or 16 of PU-foam. The two 1-2 mm thick intermediate layers 15, 16 embed the sheet and form a first padding/cushioning. Cover layers 18 and 17 are arranged over the intermediate layers 15, 16 at the top and bottom, and are laminated together with the respective intermediate layer.

The inner cover layer 18 consists preferably of a textile material leading away sweat. It is advantageously additionally provided with a function preventing the propagation of sweat bacteria, which may be achieved by way of a special material selection or by way of an impregnation with suitable substances. By way of this, one ensures that the finger F which is splinted over a longer time is kept dry and remains free of smell. Moreover, by way of perforating the sheet 14, it is ensured that air may get to the lower side of the finger which is covered by the splint. The textile material of the cover layer 18 additionally contributes to the wearing comfort of the mallet finger splint 10 on account of its textile nature.

Figure 3:
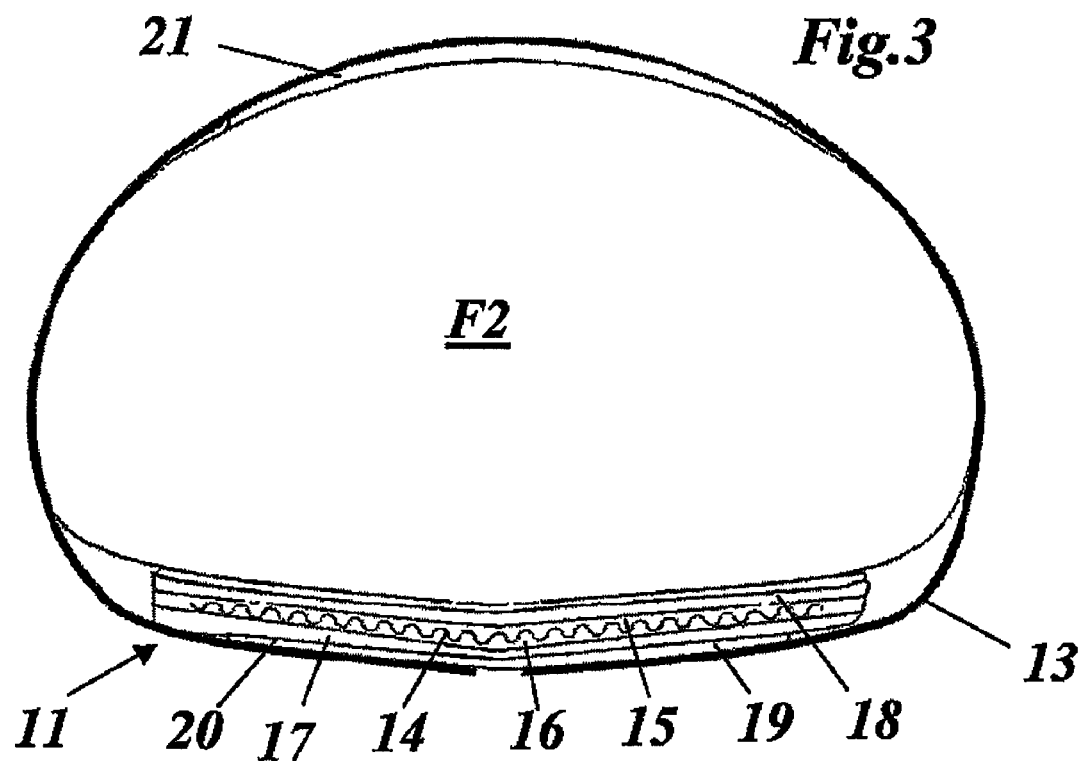
FIG. 3 the cross-section through the mallet finger splint attached on the finger, according to FIG. 2, in the region of the handle or the middle phalanx.
Figure 4:
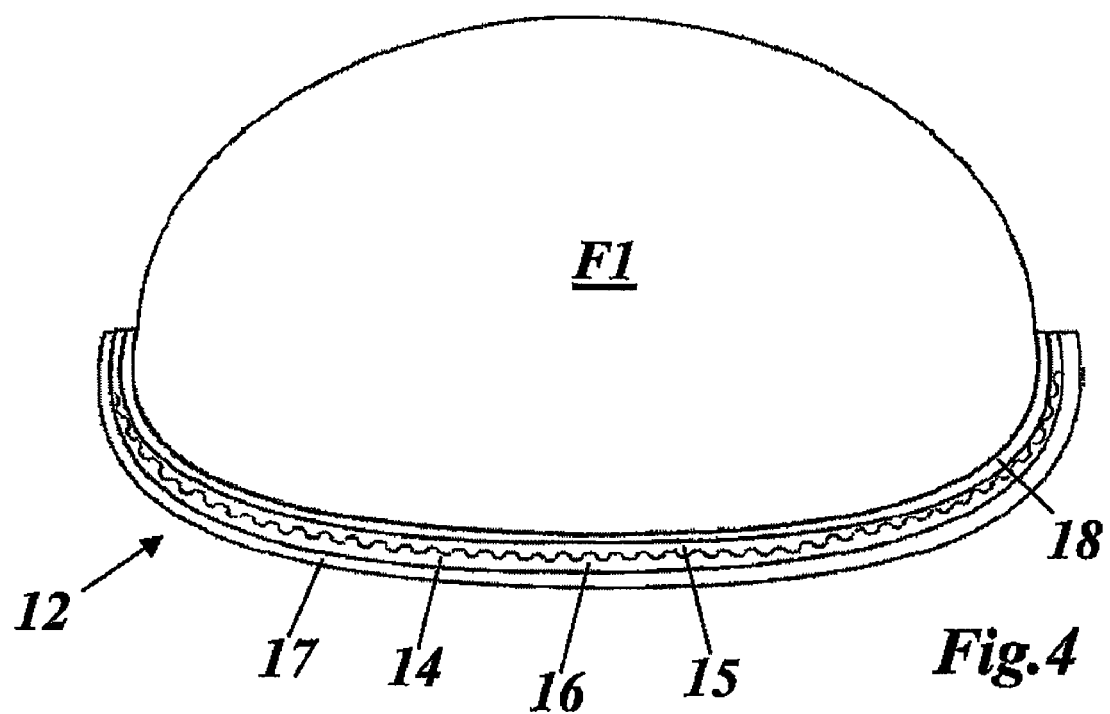
FIG. 4 in a representation comparable to FIG. 3, the cross section through the mallet finger splint attached on the finger according to FIG. 2, in the region of the shell or of the first phalanx.

The outer cover layer 17 consists of a textile material which is suitable for a Velcro-type closure and which has the character of velour or fleece, and thus may cooperate with the hook side of a Velcro-type tape in a sticking manner. A fastening tape 13 which may be wound firmly around the handle 11 and the middle (medial) phalanx F2 (FIG. 2, 3) is provided for fastening the mallet finger splint 10 on the finger F. The fastening tape 13 is fastened with both ends to the mallet finger splint 10 according to FIG. 3. For this, a Velcro-type closure is formed on the mallet finger splint 10 on the outer side or lower side of the handle 11, in that a double-sided Velcro-type strip is fastened (hooked in) with the one side on the lower cover layer 17. The other, free side of the Velcro-type strip 19, serves for the fastening of the fastening tape 13 at both ends (FIG. 3). For this, the fastening tape 13 is provided on at least one side with a suitable velour or fleece, which at the same time increases the wearing comfort.

As shown in FIG. 2, the mallet finger splint 10 with the handle 11 is firmly fastened on the middle (medial) phalanx F2, whilst the shell 12 projecting to the front supports and stabilizes the front (distal) phalanx F1 in a slightly over-extended posture. The handle 11 is kept so short, that the middle finger joint may be bent, without the free handle end abutting on the rear phalanx F3 and thus exerting a displacement force on the splint. In order to otherwise securely prevent a shifting of the mallet finger splint 10 in the longitudinal direction of the finger to the front, and thus a decrease of the support function of the shell 12, additional sticking means in the form of a double adhesive strip 20 bonded onto the upper layer 18 of the handle 11 are provided on the inner side of the handle 11, for fixing the mallet finger splint 10 relative to the finger F. The adhesive strip 20 is preferably of a fabric material, in order not to compromise the air permeability and moisture permeability in the region of the splint (breathable).

An additional fixation of the splint on the finger F may be achieved by way of a further double adhesive tape 21 on the upper side of the middle (medial) phalanx F2, by way of which the position of the fastening tape 13 is stabilized relative to the finger (FIG. 3) The double adhesive tape 21 which may likewise be breathable, for this, may be attached at a suitable location (in a middle section) on the fastening tape 13.

It is to be understood per se, that the double adhesive tapes or comparable sticking means may also be applied in an effective manner on fixation of other splints relative to the splinted member.

Figure 5:
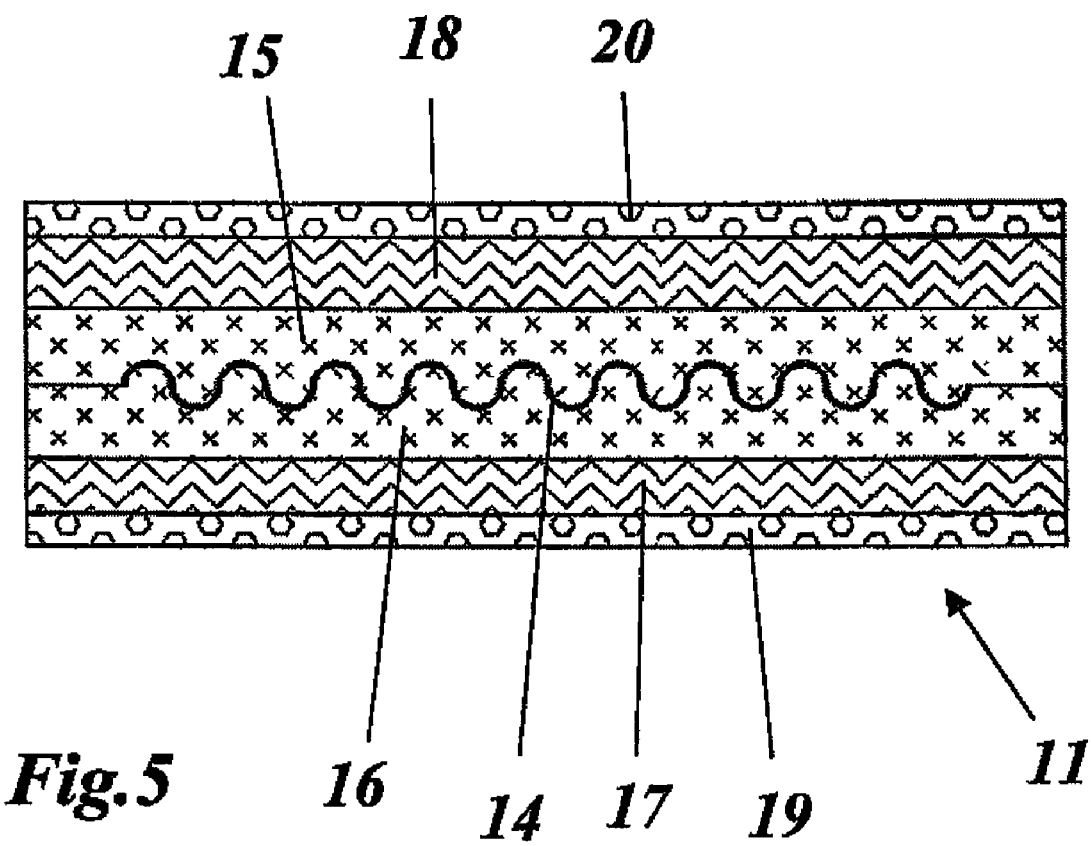
FIG. 5 an enlarged, schematic representation of the cross section of the mallet finger splint according to FIG. 1, in the region of the handle.

Within the framework of the invention however, a greatly simplified form may be applied instead of the multi-layered construction of the mallet finger splint shown in FIG. 5, with which according to FIG. 6, the mallet finger splint 10' consists of a single-piece, injected plastic part with which a hook layer 23 is formed on the lower side of the handle 11 directly on injection molding, which later serves for fastening the two ends of a fastening tape 13 (wound around the splinted finger as in FIG. 3) in the manner of a Velcro-type closure. A particularly simple construction and a particularly simple application of the mallet finger splint 10' results on account of this. Additional layers for padding and/or slippage prevention (e.g. fabric with embedded silicone balls, etc.) may be deposited on the upper side 22 of the mallet finger splint 10', wherein these are not represented in FIG. 6. The hook layer 23 may however also be bonded onto the lower side of the handle 11.

Figure 8:
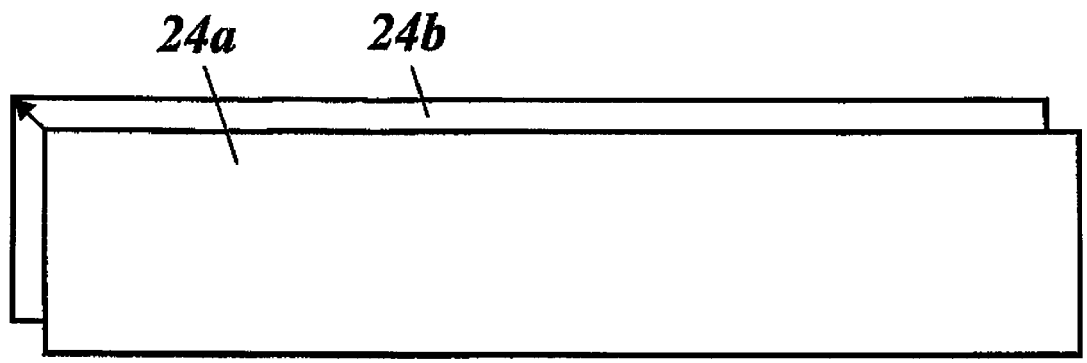
FIG. 8-10 different steps on manufacture of a mallet finger splint according to FIG. 7, according to one embodiment example of the invention.
Figure 9:
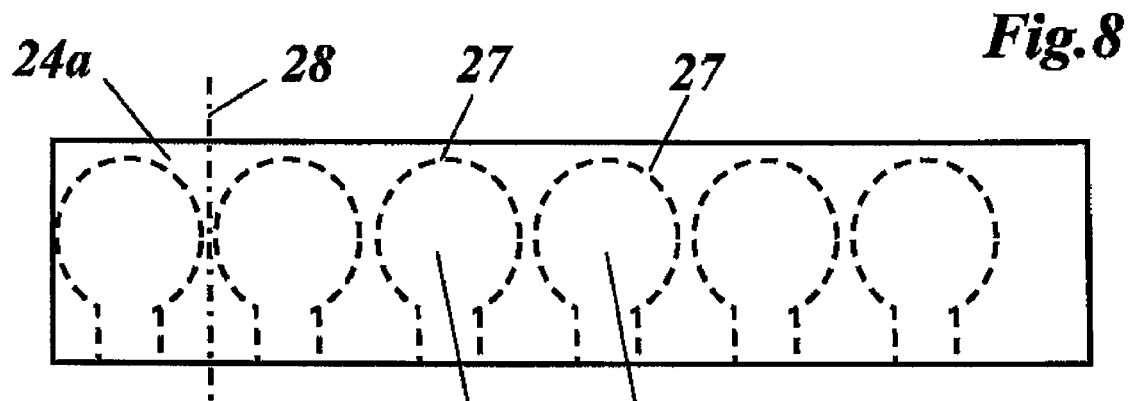
Figure 10:
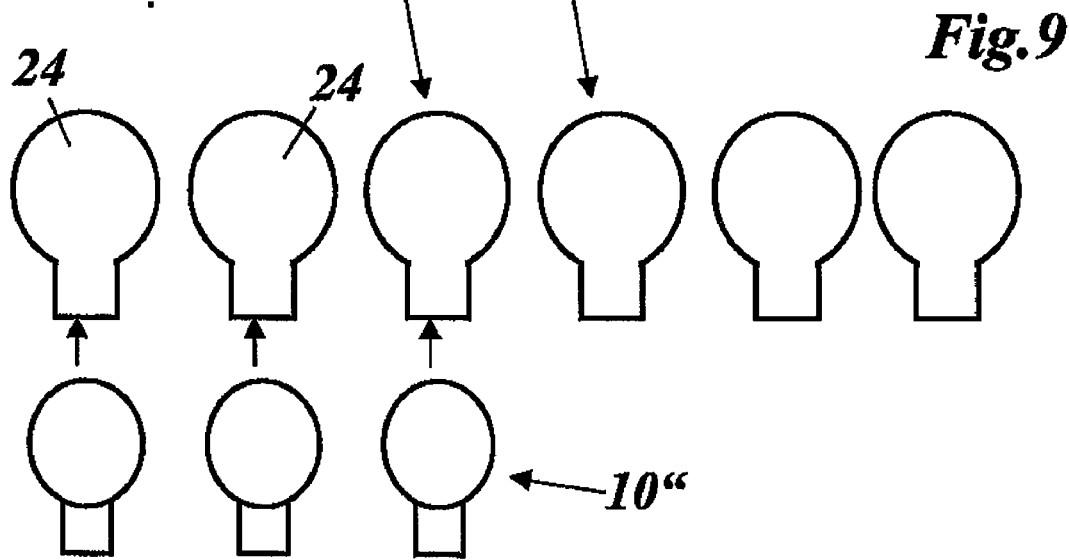

One further possibility of being able to manufacture a simple mallet finger splint inexpensively in large scale production within the framework of the invention, may be explained by way of FIGS. 7 and 8-10. Firstly, sheaths 24 open at one side are manufactured of two strip-like plies 24a, 24b of different material, into which sheath the premanufactured mallet finger splints 10" with a spoon shape may be inserted (FIG. 10). The construction and material selection of the mallet finger splints 10" may be selected within a broad scope. The sheaths 24 are designed such that depending on requirements, they may fulfill the necessary functions (padding, absorbing sweat, preventing or securing slipping, etc.) on the upper side which faces the splinted finger, and, on the lower side, at least in the region of the handle 11, they serve for the releasable fastening of the ends of the fastening tape 13.

The upper ply 24a and the lower ply 24b are applied over one another according to FIG. 8, and are connected amongst one another along the connection contours 27 which are shown dashed in FIG. 9 and which correspond to the edge contours of the mallet finger splints 10". Thereby, one side remains open for inserting the splint. The connection seams between the upper ply 24a and the lower ply 24b (25, 26 in FIG. 7) may be produced by way of sewing, bonding, sealing or in another manner. The individual sheaths 24 (FIG. 10) remain after the separation of the ply composite 24a, 24b along separation lines 28 and the removal of the excess composite material. The mallet finger splints 10" are then inserted into the elastically extendable individual sheaths 24 (FIG. 10), and the sheaths 24 are then subsequently closed and/or connected or bonded to the splint.

A configuration as is represented in a simplified manner in FIG. 7 results in cross section in the region of the handle 11. The upper ply 24a comes into contact with the finger on splinting. The material of the upper ply 24a, for example a skin-friendly fabric, should be selected accordingly. In particular, means for securing against a slippage of the finger relative to the splint may be provided in the upper ply 24a. In particular, balls of silicone which are incorporated into the fabric and act as slippage-blockers, are suitable for this. The lower ply 24b may be advantageously used for fastening the ends of the fastening tape 13, in that it is provided with a hook-like surface in the manner of a Velcro-type closure, at least in the region of the handle 11. A very simple application of the finger splint arises on account of this, as well as a very simple and flexible construction and a high wearing comfort. The finger splint may simultaneously be produced in an inexpensive manner and in a large-scale manner. The upper ply and lower ply 24a,b may however also fulfill further additional functions given a suitable material selection.

LIST OF REFERENCE NUMERALS 10, 10', 10" mallet finger splint
11 handle
12 shell
13 fastening tape
14 sheet (Al, corrugated)
15, 16 intermediate layer (PU-foam)
17 outer cover layer (fleece)
18 inner cover layer (lining)
19 Velcro-type tape (double-sided)
20, 21 adhesive strips (double-sided)
22 upper side (handle)
23 hook layer
24 sheath
24a upper ply
24b lower ply
25, 26 connection seam
27 connection contour
28 separating line
29 front (distal) finger joint
30 middle fingerjoint
F finger
F1, . . . , F3 phalanx The inventon claimed is:

1. A mallet finger splint for splinting two front phalanxes of a mallet finger in a position in which a front finger joint is held in an extended position between a front (distal) phalanx and a middle (medial) phalanx, the mallet finger splint comprising;
   a shape of a spoon with a handle and a shell such that the handle lies below the middle (medial) phalanx, whilst the front (distal) phalanx comes to lie in the shell, and wherein a length of the handle is adapted to a length of the middle (medial) phalanx such that the middle finger joint is freely movable;
   the mallet finger splint formed as one piece comprising an aluminum sheet that is plastically deformable by hand, the aluminum sheet including:
     corrugations formed therein for longitudinal stiffening, whose crests run in the longitudinal direction of the splint or of the finger;
     perforations formed therein for improving breathing activity,
     an intermediate layer of PU-foam covering on both inner and outer sides of the mallet finger splint, and
     a further cover layer arranged on the intermediate layers, the intermediate layers bonded to the aluminum sheet metal, and the intermediate layers and the associated cover layers are in each case laminated together.

2. A mallet finger splint according to claim 1, wherein the inner cover layer consists of a textile material leading away sweat, and the outer cover layer includes a textile material which is suitable for a Velcro-type closure.

3. A mallet finger splint according to claim 2, wherein the inner cover layer is additionally provided with a function preventing the formation of sweat bacteria.

4. A mallet finger splint for splinting two front phalanxes of a mallet finger in a position in which a front finger joint is held in an extended position between a front (distal) phalanx and a middle (medial) phalanx, the mallet finger splint comprising:
   a shape of a spoon with a handle and a shell such that the handle lies below the middle (medial) phalanx, whilst the front (distal) phalanx comes to lie in the shell, and wherein a length of the handle is adapted to a length of the middle (medial) phalanx such that the middle finger joint is freely movable; and
   a double adhesive strip bonded onto an upper layer of the handle to prevent relative displacement between the mallet finger splint and the finger.

5. A mallet finger splint for splinting two front phalanxes of a mallet finger in a position in which a front finger joint is held in an extended position between a front (distal) phalanx and a middle (medial) phalanx, the mallet finger splint comprising a shape of a spoon with a handle and a shell such that the handle lies below the middle (medial) phalanx, whilst the front (distal) phalanx comes to lie in the shell, and wherein a length of the handle is adapted to a length of the middle (medial) phalanx such that the middle finger joint is freely movable; and a sheath, wherein the sheath further comprises:
  an upper ply; and
  a lower ply, wherein the finger to be splinted comes to lie on the upper ply, and the lower ply covers the mallet finger splint on the lower side, the upper ply including slippage-preventing silicone in the form of embedded balls, wherein the lower ply is formed as part of a Velcro-type closure containing hooks.

* * * * *